United States Patent [19]
Husain

[11] Patent Number: 5,867,831
[45] Date of Patent: Feb. 9, 1999

[54] EXAMINATION GLOVE WITH PALPABLE MARKINGS

[76] Inventor: Abbas M. Husain, 8 Bunning Dr., Voorhees, N.J. 08043

[21] Appl. No.: 847,942

[22] Filed: Apr. 28, 1997

[51] Int. Cl.[6] .................................................. A41D 19/00
[52] U.S. Cl. ..................................... 2/161.7; 2/163; 2/168
[58] Field of Search ........................... 2/161.7, 163, 168, 2/159, 160, 161.1, 161.6; 606/102, 119, 148, 204; 600/591, 593, 588, 587; 33/512

[56] References Cited

U.S. PATENT DOCUMENTS

| | | | |
|---|---|---|---|
| 1,279,855 | 9/1918 | Garvey | 2/168 |
| 2,036,413 | 4/1936 | Herbruck | 2/168 |
| 2,394,140 | 2/1946 | Biscow | 128/361 |
| 3,283,338 | 11/1966 | Landau | 2/168 |
| 3,643,651 | 2/1972 | Cuadrso | 128/2 S |
| 4,611,603 | 9/1986 | Kelso et al. | 128/775 |
| 5,323,490 | 6/1994 | Yarbrough | 2/161.7 |
| 5,421,033 | 6/1995 | DeLeo | 2/161.7 |
| 5,423,090 | 6/1995 | Gimbel | 2/168 |
| 5,442,816 | 8/1995 | Seketa | 2/161.7 |
| 5,448,777 | 9/1995 | Lew | 2/161.7 |
| 5,496,337 | 3/1996 | Brown | 2/163 |

FOREIGN PATENT DOCUMENTS

| | | | |
|---|---|---|---|
| 796667 | 4/1936 | France | 2/163 |

*Primary Examiner*—Amy B. Vanatta
*Attorney, Agent, or Firm*—Robert D. Thompson, Esquire

[57] ABSTRACT

The present invention is a device to enable a physician to accurately measure masses encountered during rectal, pelvic, surgical or other internal examinations where the examiner cannot see the objects but must judge their size by only palpitation. The device comprises a one-piece tight fitting glove of thin elastic impervious material with four fingers and a thumb with palpable markings located on one or more fingers of the glove. The markings are spaced at intervals of known length between the interphalangeal joint and the tips of one or more fingers on the pad or palm side, and can be felt on the inside of the glove such that the physician can accurately measure masses which he or she is able to feel but cannot observe.

5 Claims, 2 Drawing Sheets

EXAMINATION GLOVE WITH PALPABLE MARKINGS

FIELD OF INVENTION

Tight fitting flexible gloves are used by a physician in medical examinations. In the case of internal examinations such as rectal or pelvic examinations, the physician must often make judgments about the sizes of objects that can be felt but not seen during the examination. This invention discloses an examination glove that facilitates better quantitative judgments about sizes of objects felt through the glove.

BACKGROUND AND OBJECTIVES OF INVENTION

An important part of every physical examination and even during surgery is the examiner's ability to correctly evaluate the size of internal masses to determine whether there is an abnormality regarding the size of the mass or if it has grown since the previous examination. Rectal, pelvic, surgical or other examinations are, in most instances, done without the ability to see the area under examination and assess sizes of masses except by palpitation (feel). The present invention provides a means to enhance the examiner's ability to judge sizes of objects encountered during examination. The objectives of the invention are:

(1) to provide a measuring scale on an examination glove for an examiner to better judge sizes of objects by palpitation;

(2) to allow an examiner to keep numerical records of sizes observed during an examination to facilitate determination of changes from a previous examination;

(3) to cause the examiner to make more careful observations during an examination because the examiner's use of the invention to make size judgments slows the examination.

SUMMARY OF THE INVENTION

The present invention provides a means for more accurately measuring the sizes of masses encountered by an examiner during rectal, pelvic, surgical or other internal examinations wherein the examiner cannot see objects but must judge them by only palpitation. The device is comprised of a surgical or examination glove that has two or more palpable markings between the distal interphalangeal joint and the tip on the pad or palm side of the index and possibly other fingers of the glove. The distance between the markings is a specified value or values, chosen such that they can be distinguished by the natural sensitivity at the surface of the examiner's finger. The examiner uses these markings as a measuring scale during an examination so that numerical reading of sizes of masses becomes possible.

BRIEF DESCRIPTION OF THE DRAWINGS

A more complete understanding of the invention and its advantages will be apparent from the detailed description taken in conjunction with the accompanying drawings in which.

DETAILED DESCRIPTION OF THE INVENTION

Figure 1:
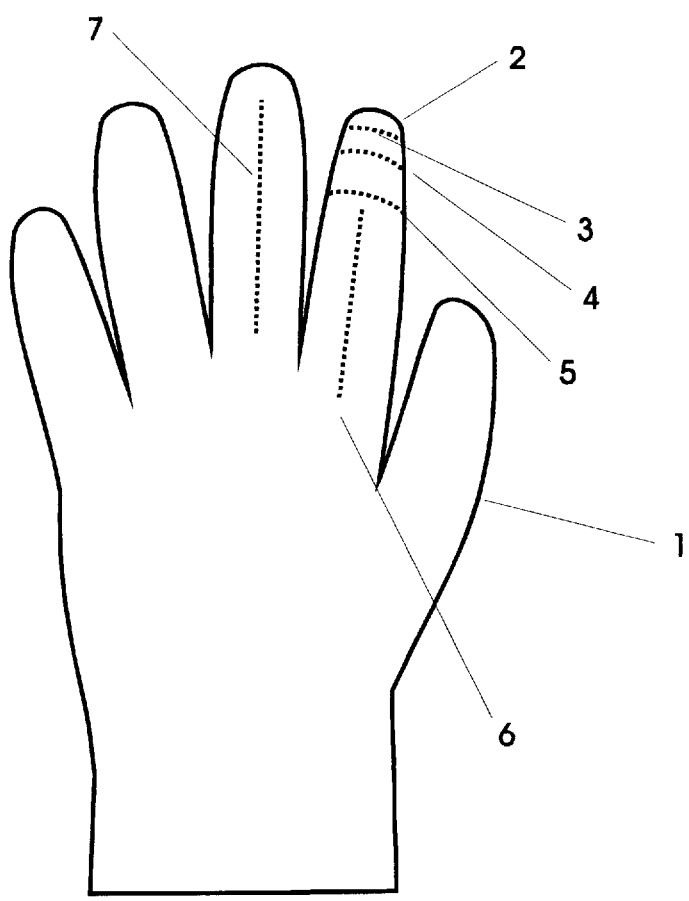
FIG. 1 is a drawing of an examination glove showing one embodiment of the invention.

A more complete understanding of the invention and its advantages will be apparent by consideration of FIG. 1. The glove 1 is fabricated from an elastic and impervious material that provides protection for an examiner's hand while not seriously inhibiting the sense of feel. The invention specifies two or more markings as shown as 3, 4 and 5 between the distal interphalangeal joint and the tip on the pad or palm side of the index finger 2.

The markings may take the form of lined indentations or bumps on either the inner, outer or both surfaces of the glove, such that they can be distinctly felt by the examiner during the examination, but not so prominent such that they would interfere with an examination or disturb the patient. Suitable markings can be fabricated on finished gloves by applying lines of cyanoacrylate or silicone material but it will be most effective to incorporate the molding of the markings into the original manufacture of the gloves.

The marking lines are spaced along the finger or fingers between the distal interphalangeal joint and the tip of the finger at specific distances on the pad or palm side of the finger of the glove such that the examiner will be able to distinguish by feel. Research [reference: Liechty, R. D. and Soper, R. T., *Synopsis of Surgery, Third Edition*, G. V. Mosby, St. Louis, 1976, p. 805] has shown that the fingertips can normally distinguish two points separated by 2 to 4 mm. Appropriate spacings of the markings for this invention are in the range of 5 to 10 mm. To further facilitate the examiner's recognition of the individual markings, it may be desirable for the separate markings to have a different feel as making each marking a different width or having one or more markings in the form of a dotted line. Additional vertical markings 6 and 7 may be useful to facilitate proper alignment of the glove and finger during use.

In use, the markings serve for palpable measurement in much the same way that one uses a visual ruler or scale. As the finger is moved over an object to be measured, the examiner can compare the size of the object to the distance between two or more of the markings on the glove. The examiner can determine if the object is smaller or larger than the distances between the markings.

Figure 2:
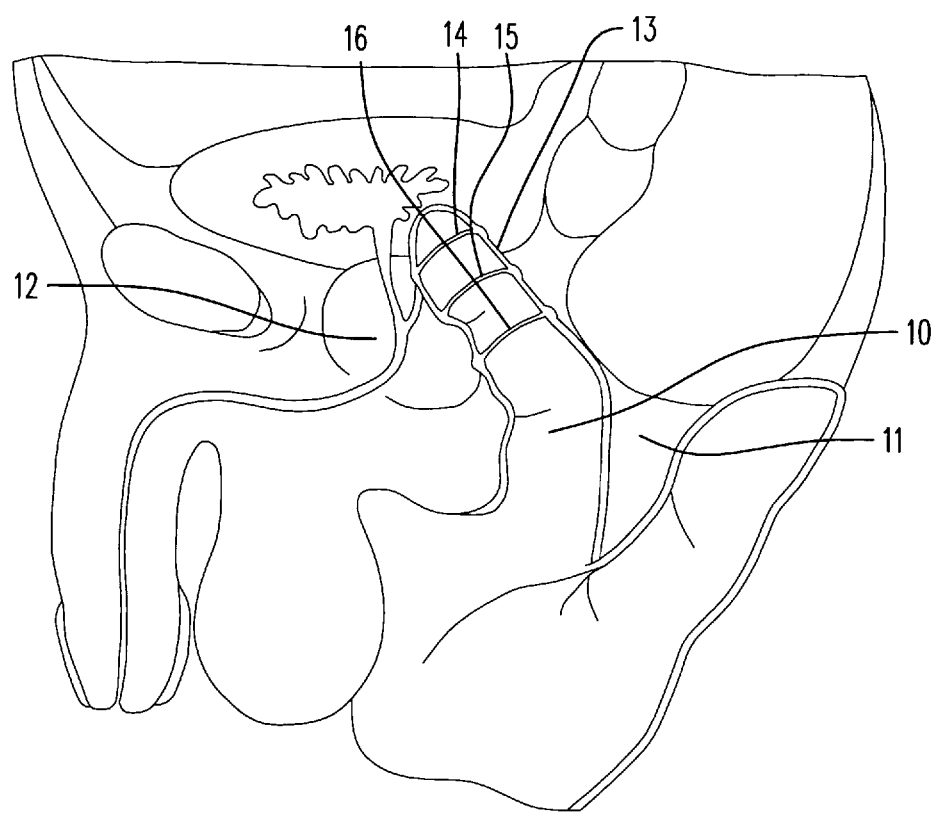
FIG. 2 is a drawing showing the glove in use for prostate examination.

FIG. 2 shows the use of the invention for a rectal examination of the prostate. In this examination, the examiner inserts a gloved finger 10 into the rectal opening 11 of the patient to evaluate the prostate 12, which is located just inside the rectum to the front. During the examination, the tight-fitting elastic glove 13 protects the patient and examiner without restricting the examiner's sense of feel. To complete the examination, the examiner locates the prostate as a mass adjacent to the rectal wall and attempts to evaluate its firmness, texture and size. A normal size of prostate under examination is about 25 mm. However, an enlarged prostate can be several times this value. By comparing the prostate size to the distance between the glove markings 14, 15 and 16, the examiner is able to make a quantitative evaluation of size. In the example of FIG. 2, the examiner would judge the prostate size to be about the same as the distance between markings 14 and 16 on the glove. With the three markings each 5–10 mm apart, this would indicate that this prostate size is 25 mm.

The example of FIG. 2 shows a prostate examination but it will be understood that the invention is applicable to all internal evaluations during surgical procedures, pelvic examinations, or any where an examiner needs to determine the sizes of internal objects.

Although this invention has been disclosed and illustrated with reference to a particular embodiment for medical examinations, the principles involved are susceptible for use in numerous other situations, which will be apparent to persons skilled in the art. The invention is, therefore, to be limited only as indicated by the scope of the appended claims.

What is claimed is:

1. A one-piece tight fitting glove constituted of thin elastic impervious material with four fingers and a thumb, one or more fingers of said glove each having a plurality of palpable markings at specified intervals between the distal interphalangeal joint and the tip of pad or palm side of the finger or fingers, said palpable markings fabricated so that they can be felt by the wearer of the glove.

2. In a glove constituted as set forth in claim 1, each palpable marking on a single finger fabricated differently so that the wearer of the glove can distinguish one palpable marking from another by feel.

3. In a glove constituted as set forth in claim 1, said palpable markings fabricated as nibs across the width of the finger or fingers.

4. In a glove as constituted in claim 1, said palpable markings fabricated as indentations across the width of the finger or fingers.

5. In a glove constituted as set forth in claim 1, said palpable markings fabricated as lines across the width of the finger or fingers.

\* \* \* \* \*